US008727817B2

(12) United States Patent
D'Hiver et al.

(10) Patent No.: US 8,727,817 B2
(45) Date of Patent: May 20, 2014

(54) SCREWLESS QUICK SYSTEM FOR CONNECTING A LEAD CONNECTOR TO A GENERATOR OF AN IMPLANTABLE MEDICAL DEVICE

(75) Inventors: Philippe D'Hiver, Chatillon (FR); Stéphane Degieux, Sceaux (FR)

(73) Assignee: Sorin CRM S.A.S., Clamart Cedex (FR)

(*) Notice: Subject to any disclaimer, the term of this patent is extended or adjusted under 35 U.S.C. 154(b) by 458 days.

(21) Appl. No.: 13/100,634

(22) Filed: May 4, 2011

(65) Prior Publication Data

US 2011/0275253 A1 Nov. 10, 2011

(30) Foreign Application Priority Data

May 4, 2010 (FR) ...................................... 10 53446

(51) Int. Cl.
*H01R 4/40* (2006.01)
(52) U.S. Cl.
USPC ...................................................... 439/789
(58) Field of Classification Search
USPC ...................................................... 439/789
See application file for complete search history.

(56) References Cited

U.S. PATENT DOCUMENTS

| 845,268 | A | * | 2/1907 | Shade | 439/828 |
|---|---|---|---|---|---|
| 1,005,283 | A | * | 10/1911 | Neher | 439/787 |
| 1,363,350 | A | * | 12/1920 | Recker | 439/786 |
| 1,661,124 | A | * | 2/1928 | Koretzky | 439/828 |
| 2,027,220 | A | * | 1/1936 | Benson | 439/786 |
| 2,222,715 | A | * | 11/1940 | Kuhlman | 439/269.2 |
| 2,528,121 | A | * | 10/1950 | Dickinson | 439/269.2 |
| 3,477,060 | A | * | 11/1969 | Lawlor | 439/789 |
| 3,596,229 | A | * | 7/1971 | Hohorst | 439/592 |
| 3,984,655 | A | * | 10/1976 | Wahl | 219/233 |
| 4,245,642 | A | * | 1/1981 | Skubitz et al. | 607/37 |
| 4,311,359 | A | * | 1/1982 | Keller | 385/88 |

(Continued)

FOREIGN PATENT DOCUMENTS

| EP | 0890371 | | 1/1999 |
|---|---|---|---|
| EP | 900577 | * | 2/1999 |
| EP | 0900577 | | 3/1999 |
| FR | 2662310 | | 11/1991 |

OTHER PUBLICATIONS

Foreign Search Report (Annexe Au Rapport De Recherche Preliminaire Relatif A La Demande De Brevet Francais No. FR0958137 FA730043), Feb. 14, 2011.

*Primary Examiner* — Neil Abrams
(74) *Attorney, Agent, or Firm* — Foley & Lardner LLP

(57) ABSTRACT

A screwless quick connection system for connecting a lead connector to a generator of an active implantable medical device. The connector head includes a housing (16, 18) receiving a plug (22) of a lead connector. A mechanism for locking the plug into the housing is provided by a U-folded leaf spring (30). Each branch of the U is provided with a respective hole sized so that the plug (22) passes through the holes on both branches when it is inserted into the housing. The blade is deformable between a free state, in the absence of plug, and a deformed state, with the plug inserted therein. In the free state, both holes are misaligned, while in the deformed state they are aligned. In this way, an edge of both holes exerts by reaction a radial stress force against the smooth outer surface of the plug inserted therein. A pushbutton flange (40) unlocks the system by a support maneuver on only one side of the connector head.

17 Claims, 3 Drawing Sheets

(56) References Cited

U.S. PATENT DOCUMENTS

| | | | | |
|---|---|---|---|---|
| 4,347,849 A | * | 9/1982 | Congdon | 607/37 |
| 4,410,228 A | * | 10/1983 | Stephenson | 439/436 |
| 4,708,417 A | * | 11/1987 | Woertz | 439/828 |
| 5,252,090 A | | 10/1993 | Giurtino et al. | |
| 5,275,620 A | | 1/1994 | Darby et al. | |
| 5,421,749 A | * | 6/1995 | Schrauder | 439/786 |
| 5,885,116 A | * | 3/1999 | Byfield, Jr. | 439/759 |
| 5,919,065 A | * | 7/1999 | Warner et al. | 439/789 |
| 5,993,244 A | * | 11/1999 | Bechaz et al. | 439/417 |
| 6,112,120 A | | 8/2000 | Correas | |
| 6,134,917 A | * | 10/2000 | Kohl et al. | 63/12 |
| 6,196,883 B1 | * | 3/2001 | Bechaz et al. | 439/789 |
| 6,264,498 B1 | * | 7/2001 | Froberg | 439/441 |
| 6,312,297 B1 | * | 11/2001 | Lorkowski | 439/838 |
| 6,487,430 B1 | * | 11/2002 | Henderson et al. | 600/394 |
| 6,783,385 B2 | * | 8/2004 | Rudy | 439/438 |
| 7,234,981 B2 | * | 6/2007 | Eppe et al. | 439/834 |
| 7,607,953 B2 | * | 10/2009 | Fabian | 439/789 |
| 7,892,017 B2 | * | 2/2011 | Meyer et al. | 439/435 |

* cited by examiner

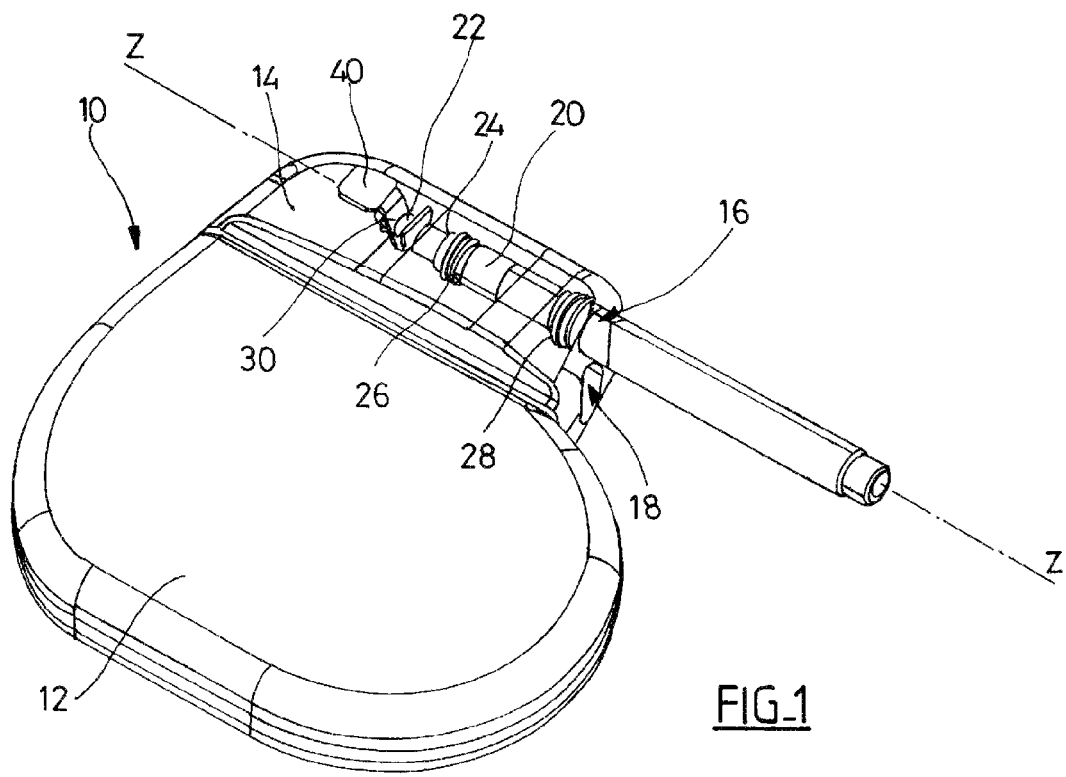
FIG_1
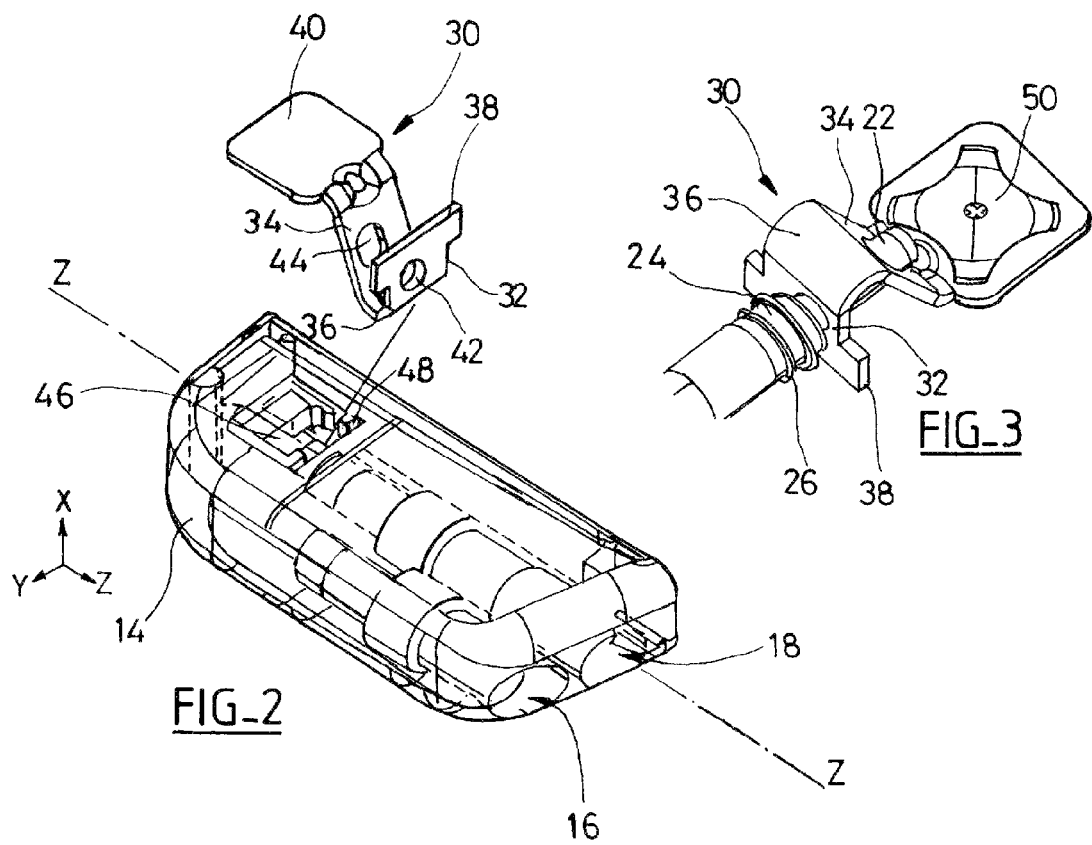
FIG_2
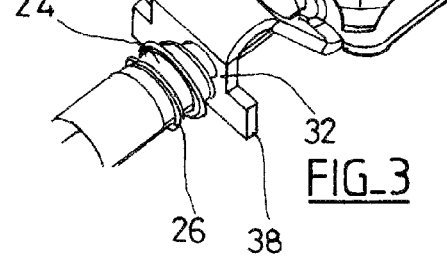
FIG_3

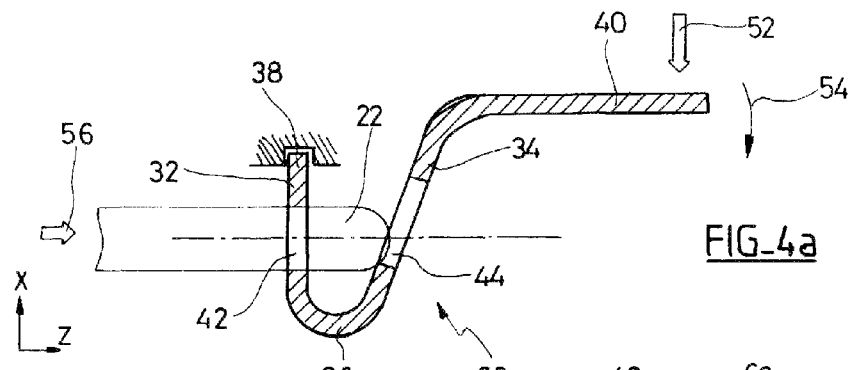
FIG_4a
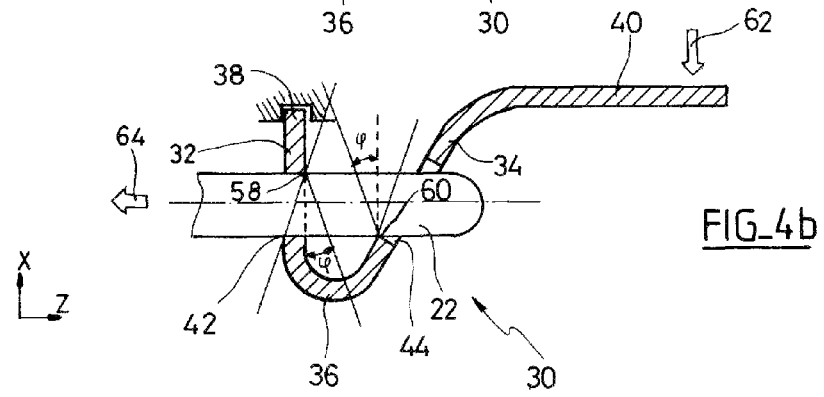
FIG_4b
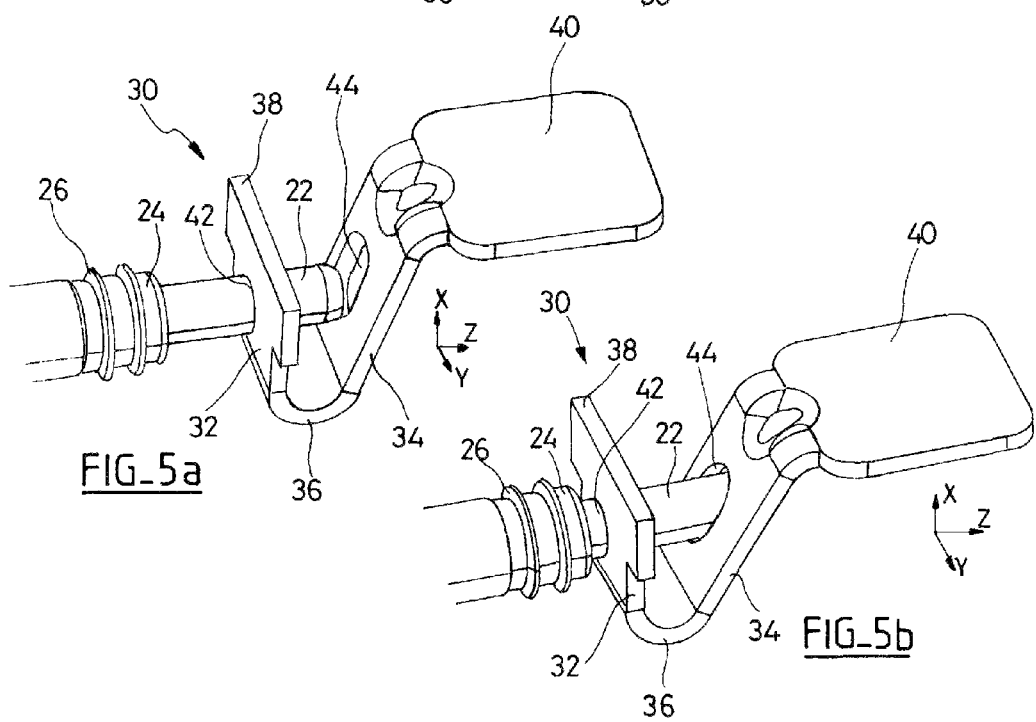
FIG_5a
FIG_5b

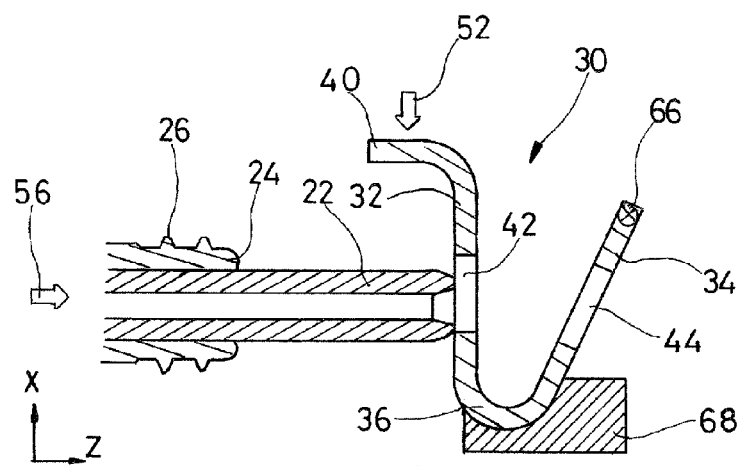
FIG_6a
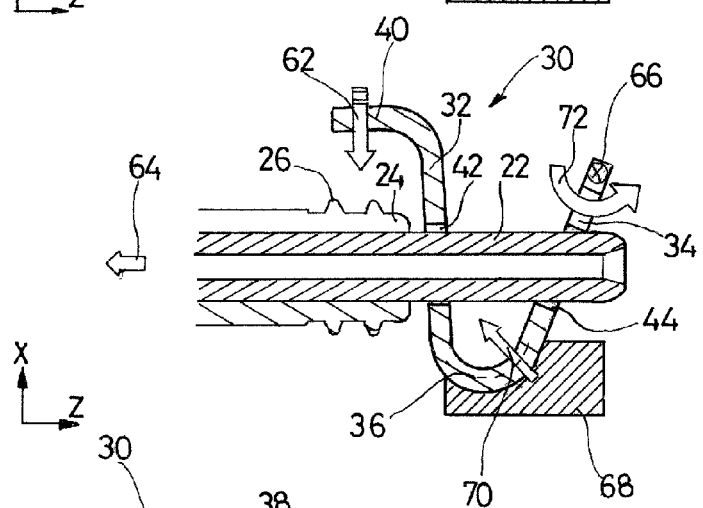
FIG_6b
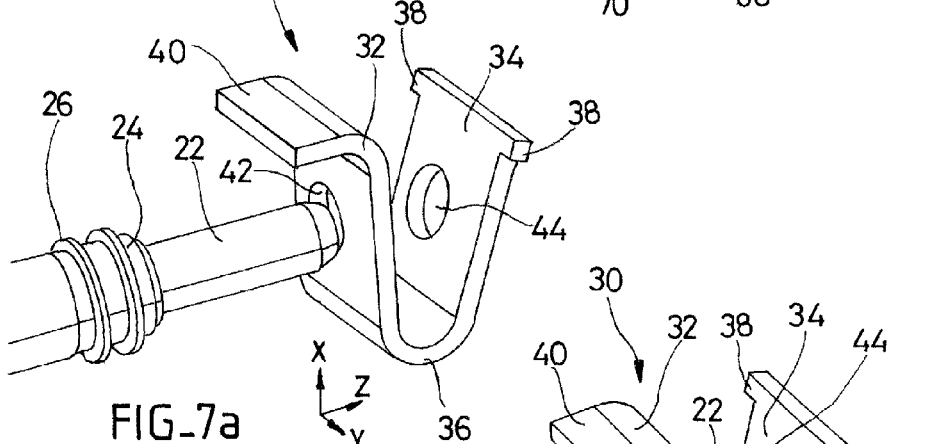
FIG_7a
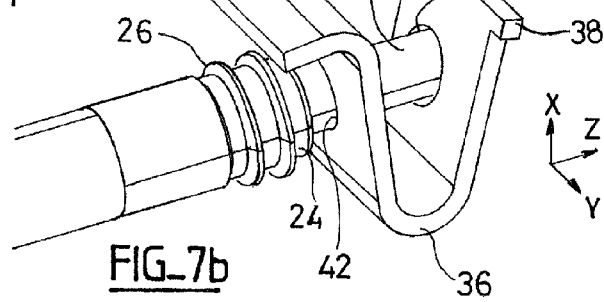
FIG_7b

SCREWLESS QUICK SYSTEM FOR CONNECTING A LEAD CONNECTOR TO A GENERATOR OF AN IMPLANTABLE MEDICAL DEVICE

The present application claims the benefit of French application Ser. No. 10/53446 entitled "Screwless Quick Connection System Of A Lead Connector To A Generator Of An Implantable Medical Device" and filed May 4, 2010, which is hereby incorporated by reference in its entirety.

FIELD

The present invention relates to an active implantable medical device as defined by the Jun. 20, 1990 directive 90/395/CEE of the European Community Council, including those devices that continuously monitor a patient's cardiac activity and, if necessary, deliver to the heart electrical pulses for stimulation, cardiac resynchronization, cardioversion and/or defibrillation, in response to a rhythm disorder detected by the device, and those devices such as neurological devices, cochlear implants, drug pumps, and implanted biological sensors.

BACKGROUND

Active implantable medical devices include a housing that is generally designated as "the generator." The generator is mechanically and electrically connected to one or more "leads" that bear on them one or more electrodes that contact those tissues to which it is desirable to deliver electrical pulses, e.g., to apply stimulation pacing pulses, and/or to collect (detect) an electrical signal. These tissues include, for example, myocardial, nerve, and muscle tissue.

The French standard NF EN 50077 and its international counterpart ISO 5841-3, Implants for Surgery—Cardiac Pacemakers—Part 3: Low-Profile Connectors (IS-1) for Implantable Pacemakers, defines a normalized connection system standard in the industry, which is identified as "IS-1". The IS-1 standard ensures interchangeability and compatibility of the leads and generators produced by different manufacturers. In this regard, it should be understood that the present invention is not limited to the particular case of a connection system according to the IS-1 standard, nor even to connection systems applicable to cardiac pacemakers.

Typically, the connection between a lead connector—hereafter more simply referred to as "plug"—and a connector of a generator is made by one or more screws that are tightened by the surgeon using an ad hoc tool (e.g., a screwdriver, possibly equipped with a torque limiter) at the time of implantation of the device and/or the lead. This known screw connection system has several drawbacks. First, in addition to requiring a specific tool for its implementation, this system requires the presence of caps provided with sealed slots through which the tool must pass to prevent the terminals from coming into contact with body fluids after implantation. This requirement for sealing the slots through which the tool passes increases the cost and requires a volume or size of the generator at the connector that is large enough to accommodate the tool.

Second, a screw connection system does not prevent from a screwing oversight, whether from an insufficient screwing or from an overtightening of the screw and damaging the device, by the surgeon.

Third, a screw connection system also introduces significant risks of damage to the silicone plug by the screwdriver with a consequent loss of insulation, of removal or stripping of the screw thread at the time of its use, of binding thereof, or of damage to the head of the screw in case of incorrect insertion of the screwdriver.

From an economic standpoint, the use of a screw system generates certain additional costs (e.g., manufacturing of the screw, threading of inserts) and requires providing with the medical device a special tool (e.g., a screwdriver with torque limiter) for tightening the screw. From an industrial standpoint, the use of a screw connector system requires an operation for inserting and adjusting the position of screws in a predetermined position during the packaging of the device, and of addition of a spot of glue to freeze this position of the screw. From a safety standpoint, the operation of screwing the screw by the physician to secure the plug requires special attention, with an implementation time large enough to make sure that the plug is maintained in the housing, precisely and durably.

Despite these acknowledged drawbacks, the screw connection system is still almost universally used. Indeed, the connectivity standards related to implantable medical devices require (i) minimum retention forces sufficient to prevent accidental disconnection at the time of implantation or during the product lifetime, and (ii) a high-quality and enduring electrical contact (i.e., a very low contact resistance) between the connector plug of the lead and the electrical terminal of the implantable device. These two mechanical and electrical requirements are particularly well satisfied by a conventional screw connection system, despite its many disadvantages.

Various other systems for securing the plug into the housing of the connector head have been proposed to overcome the many difficulties and drawbacks outlined above.

Thus, EP 0890371 A1 and its counterpart U.S. Pat. No. 6,112,120, both assigned to Sorin CRM S.A.S., previously known as ELA Medical, describe separating the electrical contact and mechanical retention functions. The electrical contact is ensured by a spring system exerting a radial pressure against the conductive surface of the plug. The mechanical retention of the plug in the housing is secured by a locking wedge inserted between the body of the plug and the housing wall at the outlet thereof.

Another solution is proposed by EP 0900577 A1 (assigned to Sorin CRM S.A.S., previously known as ELA Medical), which implements a locking system with a retractable spring-loaded eccentric, locally applied against the plug and bearing against it response to an attempted extraction.

These solutions are functionally effective, but they involve relatively complex, and therefore expensive to produce, mechanical systems (e.g., including elements such as a spring, eccentric, and slide). They also require a specific release mechanism for the removal of the plug, typically requiring the use of a special tool for removing the holding or retraction force provided by the eccentric. Finally, they require special precautions to durably ensure the efficient sealing required at the connector.

Other known efforts at alternative connection systems implement deformable elastic elements such as metal blades with one or more orifices through which the plug passes when inserting it into the slot, and exerting a radial point of contact between the edge of the orifice and the surface of the plug.

Thus, U.S. Pat. No. 5,252,090 (Giurtino et al.) proposes to block the plug with an elastically deformable metal piece, extending around the plug in a plane substantially radial to the axis of the plug. Deformable tabs formed in the part produce by stemming an anti-kickback effect, preventing any withdrawal or pulling of the plug once it is inserted in the metal part. For disassembly, the part is extended laterally by two symmetrical ears that, by pinching, deforms the piece enough to remove the tabs of the plug and release it. This device is very effective in terms of mechanical retention. However, unlocking the device requires having two entrances on each side of the part, to ensure a symmetrical pinching, and therefore requires providing two release buttons (one on each side of the head connector).

FR 2 662 310 A (Darby et al.), refers to an elastic clamp whose ends of the two arms are folded against one another and are provided with holes corresponding to the diameter of the plug. The holes are shifted when the clamp is in the free state, and they can be aligned by moving the two arms of the clamp. The plug can then be introduced through the two holes, and be retained in the clamp after release of the force exerted to bring the two arms together. This connection system is very effective in terms of mechanical retention of the plug, but it is not designed to be integrated with a generator. Rather, it is presented to serve as a dispensing connector between several leads, this connector being placed away from the generator.

OBJECT AND SUMMARY

It is therefore, an objective of the present invention to provide a generator for an active implantable device including a connector head provided with a connecting system for the plug of a lead that is both simple and effective and that would:
  allow connection and disconnection of the plug to the connector terminal without screws and without ad hoc tools;
  establish a strong mechanical connection ensuring an effective and permanent retention of the plug, even in the case of plugs with smooth surfaces such as those carried out in accordance with the IS-1 standard mentioned above; and
  be integrated into the very small volume of the connector head of an implant, so as to be minimally invasive for the patient.

Broadly, the present invention is directed to a leaf spring system which, by its geometric characteristics and the nature of the material used, can provide a tool-free system for securing a plug when it is inserted into the connector housing of the generator of the device with a specific geometry for ensuring the mechanical action of locking/unlocking the plug from one only side of the generator.

One embodiment of the invention is a device in which the connector head includes, in a manner in itself known, for example, according to the FR 2 662 310 A cited above, at least one female housing provided with an electrical connection terminal and able to receive a plug, the plug having, for example, a smooth surface of a cylindrical or prismatic lead connector, and locking means for the mechanical immobilisation of the plug in the housing. The locking means preferably has a resilient member adapted to be deformed and placed under elastic tension when inserting the plug into a slot in the housing in which the resilient member is disposed. The resilient member also is adapted to be deformed after insertion of the plug, the elastic deformation then being in an axial direction, such that the resilient member comes to exert a retention force on the plug. This retention force in the radial direction exerts contact pressure against the smooth surface of the plug far exceeds the force of insertion of the plug into the housing, and opposes an extraction force applied to the plug. The device also includes structure for releasing the locking means, able to apply to the resilient member, due to an external force, a mechanical force to neutralize the retention force and thereby permit an extraction of the plug from the housing.

In one embodiment, the resilient member is a leaf spring folded to have a generally U-shaped portion including a central region at the base of the U and two legs or branches of the U extending from the central portion. A first branch preferably extends in a plane in a first direction forming a first angle with respect to an axial direction of insertion of the plug into the slot, and a second branch preferably extends in a plane in a second direction forming a second angle with respect to the axial direction of insertion. The two branches are elastically connected in the central region of the U and extend from the central region to a respective end, and each branch is provided with a respective hole sized so that the plug can pass through the holes when the plug is inserted into the slot.

The leaf spring is thus deformable between a free state or unstressed position, in the absence of a plug, and a deformed state or stressed position, with the plug inserted. In the free position, the projections of the two holes in the first and second branches in the plane perpendicular to the axial direction of insertion are overlapping but misaligned, while in the stressed position the projections are aligned, so that one edge of each hole crossed by the plug exercises, by a reaction effect of the deformed leaf spring, a radial stress force against the smooth outer surface of the plug, thereby producing said contact pressure and a retention force.

The first branch may in particular extend in a direction primarily perpendicular to the axial direction of insertion and the second branch in a direction, primarily oblique to, forming, for example, an angle between 45° and 75° from, the axial direction of insertion.

In a first embodiment, the end of one branch of the U-shaped portion is a stationary end relative to the head of the connector, and the end of the other branch is a free end that is extended by a flange which serves as a support element. In an alternate embodiment, an auxiliary elastic body may be interposed between the connector body and the central region of the U at the junction of the two branches.

In a second embodiment, the end of one of the branches of the U-shaped portion is a free end extended by a flange serving as a support element, the end of the other branch is a pivoting end moving over the head of the connector, about an axis perpendicular to the axial direction of insertion, and a resilient return member is further inserted between the connector body and the central region of the U at the junction of the two branches.

In either embodiment, the flange is advantageously a flat push-button extending in a plane generally or substantially parallel to the axial direction of insertion, which can notably extend into an internal cavity of the connector head, this cavity being isolated in a sealed manner from the outside environment. The flange may also include an element causing a tactile response to the change of state between the free and stressed positions.

Preferably, the leaf spring is a metal blade connected to a terminal for making an electrical connection, between the lead and the generator, so as to achieve simultaneous mechanical immobilization of the plug in the housing and electrical connection of this plug to the connection terminal of the generator.

Advantageously, the present invention provides a quick screwless connector system that is handled via a single support, located on only one side of the connector head (for the lock as well as for the unlock operation). Further, the present invention locking means is sealed vis-à-vis the outside world, that is to say that no bodily fluid that would promote a loss of electrical insulation or corrosion can leak into the housing through the locking means. It also is simple to manufacture and inexpensive to industrialize. In addition to providing a mechanical connection, it also provides an electrical connection between the terminal of the generator and the plug with, in this case, a sufficiently low contact resistance (in accordance with the industry standards in force for electrical contact resistance, for example, for stimulation/detection below 5 Ohms for static and below 10 Ohms for dynamic resistance, and for defibrillation below 0.5 Ohm for static and 1 Ohm for dynamic resistance), and during the useful life of the product. The present invention also is well suited to manual use by a doctor equipped with gloves, with appropriate forces needed to lock or unlock the plug, and a use that is not affected by the environment in which the device is used (blood medium in particular). Moreover, the invention realizes a reduction of the metal mass used, providing an improved electromagnetic compatibility of the device, and a lever arm effect of reducing the effort needed from the doctor for locking and unlocking the plug and, conversely, producing with an equal force a greater contact force between the connector and the plug, therefore less electrical resistance at the point of contact.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is an elevated perspective of a generator partially cutaway to show a lead tip for an implantable cardiac device inserted into a connection system in accordance with the present invention;

FIG. 2 is an isolated view of the connector head of the device of FIG. 1 showing in exploded view the leaf spring before introduction into the slot;

FIG. 3 is a detail view in perspective of the underside of the leaf spring of FIG. 1;

FIG. 4*a* and FIG. 4*b* illustrate a first embodiment of the present invention showing the leaf spring in the free state at the beginning of introduction of the plug, and the deformed state once the plug is completely inserted and stressed into place by the leaf spring, respectively;

FIG. 5*a* and FIG. 5*b* are perspective views corresponding to respective configurations of FIG. 4*a* and FIG. 4*b*;

FIG. 6*a* and FIG. 6*b* are similar to FIG. 4*a* and FIG. 4*b*, for a second embodiment of the present invention; and FIG. 7*a* and FIG. 7*b* are counterparts of FIG. 5*a* and FIG. 5*b*, for the second embodiment of the invention.

DETAILED DESCRIPTION

Preferred embodiments of a device according to the present invention will now be described with reference to FIGS. 1-7.

In FIG. 1, reference 10 generally designates a generator of the device, a cardiac pacemaker given here as an example of any device to implement the teachings of the invention.

Generator 10 includes a body 12 enclosing the various electronic circuits and power source (e.g., a battery), coupled with a connector head 14. In the example shown, connector head 14 is intended to accommodate two different leads and therefore contain the connection terminals (not shown) having conductive elements embedded in the insulating body of the connector head 14, for example, made of epoxy resin.

To allow insertion of lead tips, each of which comprising electrical connection elements, the connector head 14 includes female housings or slots 16, 18 (also visible in FIG. 2) in which the proximal end 20 of the lead is introduced, as shown in FIG. 1.

The lead is, e.g., a bipolar lead including a lead according to the IS-1 standard mentioned above. This lead has at its distal end 20 a first smooth and cylindrical conductive surface 22, herein simply referred to as "plug". This plug is protected by a first insulating sheath 24 (also shown in FIG. 3) with peripheral reliefs 26 and 28 to ensure a sealing function vis-à-vis the external environment when the end of the lead is fully inserted into the corresponding slot 16 of connector head 14. In the case of a bipolar lead, the end 20 carries a second conductive surface, coaxial and shifted from the first (not shown), and protected by a second insulating sheath.

The present invention relates to the mechanical retention of the end 20 of the lead once it is fully inserted into the corresponding housing slot 16 or 18. It should be understood, however, that the present invention is not, prima facie, the electrical connection between conductive surfaces of the plug and the connection terminals of the connector head, because these two functions can be separated. Instead, the present invention focuses on the mechanical locking of the lead end (plug) into the connector head slot. It also should be understood that the plug need not have a smooth and cylindrical conductive surface, although that is a preferred and standard construction.

Advantageously, the electrical connection and mechanical locking may be provided by a common element (e.g., a metallic blocking conductive part electrically connected to the circuits of the generator). In other words, the invention is equally applicable in the case wherein the electrical connection is provided by a separate element from the one ensuring the mechanical retention and in the case wherein the same element performs these two functions.

In the illustrated example, the mechanical retention of the lead tip 20 in its housing is ensured by the distal end, that is to say by the plug 22, an area where the diameter of the plug is the smallest. The distal end 22 is generally in the shape of a cylindrical metal surface, but the present invention can be extrapolated by a person of ordinary skill in the art to other materials, conductive or not, and other shapes, including prismatic shapes instead of cylindrical shapes.

Retention of the plug is secured by a leaf spring 30 shown in detail in FIG. 2, and FIG. 3, FIG. 4*a*, FIG. 4*b*, FIG. 5*a*, FIG. 5*b* (for a first embodiment) and in FIG. 6*a*, FIG. 6*b*, FIG. 7*a* and FIG. 7*b* (for a second embodiment).

This leaf spring 30 is made of an elastically deformable material, for example, a spring steel. It has a generally U-shaped geometry comprising a first branch 32, on the plug insertion side, and a second branch 34, on the opposite side, with the two branches being united by a central region 36.

The first branch 32 extends in a plane substantially normal to the Z direction of insertion of the plug (also referred to as the "Z axis of insertion"), as illustrated in FIGS. 1 and 4*b*. The end 38 of the first branch is provided with structure to immobilize it relative to the connector head, which can be, for example, pins or lugs that engage the housing. The second branch 34 is in a plane that is oblique to the Z axis of insertion, with an inclination angle of about 45° to 75°. The second branch 34 is extended at its end by a flattened surface 40, hereinafter simply designated as a "flange", extending in a plane substantially parallel to the Z axis of insertion.

The leaf spring 30 is provided with two holes whose dimensions are adapted to receive the plug 22, with a hole 42 in the first branch 32 and a hole 44 in the second branch 34 located approximately vis-à-vis the hole 42. In a preferred embodiment, the hole 42 (on the branch 32 approximately normal to the axis of insertion) is a circular hole whose dimensions correspond to the diameter of the plug 22, except for the dimensional tolerances. For example, for an IS-1 distal plug, the dimension is 1.59+/−0.03 mm, and for a DF1 distal plug, the dimension is 1.25+/−0.03 mm. The hole 34 (the second branch 44 which extends obliquely to the Z axis of insertion) is an oblong hole, so that it can also be crossed, except the dimensional tolerances, by the plug inserted along the Z axis of insertion.

As can be seen in greater detail in FIG. 4a and FIG. 4b, the holes 42 and 44 are slightly shifted with respect to each other when the leaf spring is in the free state, that is to say in the absence of any external forces and before insertion of the plug 22 (see FIG. 4a). However, these holes are aligned when the plug is inserted, the leaf spring 30 then being in a deformed state of elastic stress (see in FIG. 4b). This alignment of the holes geometrically defines a channel through which the cylindrical plug 22 can be inserted, housed and kept in place.

The leaf spring 30 may be made by folding of a metal strip or blade of constant or variable thickness, with a sheet thickness typically between 0.4 and 0.6 mm. A variable thickness allows taking advantage of the relative stiffness differences associated with the different thicknesses of leaf spring 30. The various cuts, including holes 42 and 44, are preferably made in the metal blade which it is flat and the metal blade is then folded into the desired U-shape and inspected (e.g., for proper stiffness, and position of holes). The bending radius of the central region 36 and of the region connecting the second leg 34 to the flange 40 is preferably about 1.5 times the thickness at this location. It is also possible to stamp some zones to locally stiffen the metal structure. The material used is preferably a medical implantable grade material, e.g., a 316 LVM stainless steel or titanium.

The metal blade thus produced is introduced into a cavity 46 formed in the connector head 14, the latter being preferably made by molding a medical implantable grade polymer material, e.g., Tecothane (trademark) 1075 DM. The molding can directly form the cavity 46 which opens into one of the two housings 16, 18 for receiving the plug, providing also a groove 48 receiving the lugs 38 of the end of the first branch 32 of the leaf spring 30. These grooves can thus secure this end, further providing guidance, direction and positioning of the leaf spring 30 in the connector head 14.

Alternatively, instead of mounting the leaf spring 30 in the polymer block of the connector head, it is possible to mount it in an intermediate part, for example, a shaped cage, which will later be incorporated in and/or bonded to a proper location of the connector head.

To ensure sealing after placement of the leaf spring 30, the housing 46 is sealed by a flexible cover (not shown) of elastomer or plastic, secured to the connector head 14 by known techniques. For example, a seal of silicone adhesive can be deposited at the interface between the connector head 14 and the flexible cover, or the cover can be crimped using a seam framework set in the connector head or ultrasonically welded, to prevent any liquid infiltration.

The flexible cover allows the transmission of a force pressing on the flange 40 of the leaf spring 30, e.g., by a practitioner's finger. This maneuver, performed through a flexible element, eliminates any sealing problem in connection with locking/unlocking the plug.

Preferably, the connector head 14 is provided with as many cavities and leaf springs as there are lead ends to be coupled to the device. In the example shown, on one side of connector head 14 is a cavity 46 for receiving a leaf spring-blade 30 for blocking the proximal end of the lead (plug) inserted into the cavity 18. A configuration of the same type is carried on the opposite side (not visible) of the connector head to immobilize the lead tip to be inserted into the cavity 16. Thus, one of the leaf springs 30 is arranged on one side of the connector head (visible in FIG. 2), the other being disposed on the opposite lateral face (not visible in FIG. 2). The practitioner thus has two support zones with two different buttons, one on each side of the connector head, to lock/unlock either one or the other of the two lead tips, by a maneuver executed with only one finger on either side of the connector head 14.

As shown in the bottom view of FIG. 3, the flange 40 preferably comprises on one side a "tactile" device that is like a pushbutton, allowing the practitioner to feel a "click" at end of the support movement when the mechanism is sufficiently engaged, and another "click" when he releases the pressure from the support zone of the pushbutton on flange 40.

The mechanical principle of the invention will now be explained with reference to FIG. 4a, FIG. 4b, FIG. 5a and FIG. 5b, as part of a first embodiment (corresponding to FIGS. 1-3 described above).

The principle of tightening results of the deformation of the leaf spring 30: by exerting pressure (arrow 52, FIG. 4a) on the pushbutton of flange 40, the user flexes (arrow 54, FIG. 4a) the second oblique branch 34 at an oblique angle to insertion axis Z whose end is free. This action thus aligns the oblong hole 44 of the second branch 34 and the cylindrical hole 42 of the first branch 32 disposed in a plane essentially normal to insertion axis Z. The plug 22 can then be inserted (arrow 56, FIG. 4a). In the final position corresponding to a full insertion, the pressure 52 on the pushbutton of flange 40 is released so that the leaf spring 30 tends to return to its original position, but is completely prevented due to the presence of the plug 22 through the hole 44 (configuration of FIG. 4b).

The plug 22 is thereby clamped through a process of "amplified rubbing" to control the retention force and to avoid any undesired disconnection. Specifically, the leaf spring 30 applies a normal force on the plug 22 at contact points 58 and 60 of the first branch 32 and second branch 34, respectively, thus creating the phenomenon of adhesion between the two mechanical surfaces (that of the leaf spring and that of the plug). From the point of view of statics, this configuration can be described by a friction cone of angle φ characteristic of the friction coefficient f between the two surfaces, the boundary conditions being given by f=arctan(φ). The geometry of the leaf spring blade helps maintain the plug in place because any attempt to remove the plug causes at the plug/leaf-spring interface a change of orientation of the normal force at contact points 58 and 60. Due to friction any withdrawal force in tangential projection is opposed by a greater retention force opposing the withdrawing motion.

Preferably, the geometric configuration can even cause a mechanical phenomenon of jamming the plug 22 in leaf spring 30 in case of attempted withdrawal, with such a gripping force that any movement will be effectively prevented, while maintaining the static balance of forces: whatever the intensity of external mechanical actions, the bias generated by the deformation of the leaf-spring 30 causes jamming of the plug 22. The conditions for this jamming can be calculated according to known methods, taking into account the parameters constituted by the coefficient of friction f (depending on the type of materials used), the guide length L between the two contact points 58 and 60, the diameter of the plug and the diameter of the holes 42 and 44.

The blocking of the plug by the leaf spring blade 30 is in any case reversible. In this regard, a new pressure (arrow 62, FIG. 4b) on the pushbutton of flange 40 allows for a relative movement of branch 34 and provides free passage to pull back the plug (arrow 64, FIG. 4b) or to reposition it.

In an advantageous embodiment, the elastic properties of tactile feedback device 50 described above with reference to FIG. 3 can be used to amplify by leveraging the force exerted by the leaf spring blade 30 on the plug 22 after the latter has been introduced.

Alternatively or in addition, to further increase the retention force of the leaf spring blade 30, it is possible to add to the pushbutton of flange 40 a layer of elastomer material which deforms to allow passage of the plug 22, bringing by reaction extra force at the leaf spring blade to maintain the end of the plug 22 fixed in position.

A second embodiment of the present invention is described with reference to FIG. 6a, FIG. 6b, FIG. 7a and FIG. 7b, which are counterparts of FIG. 4a, FIG. 4b, FIG. 5a and FIG. 5b. In this second embodiment, the end of the second branch 34 is not a free end, but rather one end mounted on pivot 66 in the connector head, for example, by means of two lugs 38 (visible on FIG. 7a and FIG. 7b) mounted without embedding into a corresponding homologous groove of the connector head.

The end of the first branch 32, in turn, is a free end equipped with the flange 40 on which the blocking support (arrow 52, FIG. 6b) or release support (arrow 62, FIG. 6b) will be exercised. The configuration also includes a fixed elastomer pressure cushion 68 (e.g., placed at the bottom of the cavity receiving the leaf-spring 30) and supporting the central region 36 of the U of the leaf-spring 30.

Under the effect of a pressure force (arrow 52) exerted on the first branch 32, the leaf-spring 30 pivots around the connection 66 at the opposite end of the branch, and deforms while releasing the passage of plug 22 through holes 42 and 44 along insertion axis Z.

Once the plug 22 is inserted and the force 52 is removed, the plug 22 is blocked under the force of friction at the contact points with the edges of holes 42 and 44, according to the same principle as that described above in connection with the first embodiment. The deformed elastomer cushion 68 generates a permanent opposing force that helps maintain the plug 22 tight and increases the retention force (arrow 70, FIG. 6b).

To release the plug 22, the maneuver is similar: a push (arrow 62, FIG. 6b) on the flange 40 causes, against the resisting force of the elastomer cushion 68, a pivot (arrow 72, FIG. 6b) of the leaf spring 30, which deforms again, releasing the retention force previously held on the plug 22 and allowing plug 22 to move.

One skilled in the art will appreciate that the present invention can be practiced by other than the embodiments described herein, which are provided for purposes of illustration and not of limitation.

The invention claimed is:

1. An active medical device, comprising a generator and a connector head, the connector head comprising:
at least one female housing having an electrical connection terminal for receiving a plug end of a lead along an axis of insertion;
locking means for mechanical immobilization of the plug in the housing, said locking means comprising an elastic element having a free state and a deformed state, the deformed state having said elastic element under elastic tension during insertion of the plug into the electrical connection terminal and after insertion, the deformation of the elastic element being such that along the axis of insertion the elastic element exerts a retaining force against extraction of the plug in a direction opposite to the insertion, the retaining force being greater than the force of insertion of the plug into the housing, and that, in the radial direction, exerts a contact pressure against the plug,
means for releasing the locking means by an external force on the elastic element, to neutralize said retaining force and thereby permit a removal of the plug from the housing, and
an internal cavity isolated from the external environment, wherein said elastic element is a U-shaped leaf spring having a first branch and a second branch and a central region, the first and second branches of the U being elastically connected to the central region of the U-shape with the first branch of the U extending from the central region in a direction forming a first angle to the axis of insertion, and the second branch extending from the central region forming a second angle to the axis of insertion, wherein the end of one of the first and second branches is a free end having a flange extending into the internal cavity, the first and second branches having respective first and second holes, the first and second holes having respective dimensions that allow the plug to be inserted through the first and second holes in the housing, said elastic element being deformable between:
the free state, in the absence of an inserted plug, in which the projections of the first and second holes in a plane perpendicular to the axis of insertion are overlapping but misaligned, and
the deformed state, in the presence of an inserted plug, in which the projections of the first and second holes in the plane perpendicular to the axis of insertion are aligned so that an edge of each of the first and second holes contact the plug inserted therein and exert through a reaction effect of the deformed leaf spring, a radial stress force against the plug, producing said contact pressure.

2. The device of claim 1, wherein the flange comprises a flattened pushbutton extending in a plane substantially parallel to the axis of insertion.

3. The device of claim 1, wherein the flange comprises an element causing a tactile response to the change of state between the free and deformed states.

4. The device of claim 1, wherein the end of the other of the first and second branches is a stationary end relative to the connector head.

5. The device of claim 4, wherein a resilient elastic auxiliary member is interposed between the connector head and the central region.

6. The device of claim 1, wherein:
the end of the other of the first and second branches is a moving end for pivoting, relative to the connector head, around an axis perpendicular to the axis of insertion, and
a resilient elastic member is interposed between the connector head and the central region of the U.

7. The device of claim 1, wherein the first branch extends along a plane that is substantially perpendicular to the axis of insertion.

8. The device of claim 1, wherein the second branch extends along a plane that is substantially oblique to, forming an angle in a range selected from between 45° and 75° from, the axis of insertion.

9. An active medical device, comprising a generator and a connector head, the connector head comprising:
at least one female housing having an electrical connection terminal for receiving a plug end of a lead along an axis of insertion;

locking means for mechanical immobilization of the plug in the housing, said locking means comprising an elastic element having a free state and a deformed state, the deformed state having said elastic element under elastic tension during insertion of the plug into the electrical connection terminal and after insertion, the deformation of the elastic element being such that along the axis of insertion the elastic element exerts a retaining force against extraction of the plug in a direction opposite to the insertion, the retaining force being greater than the force of insertion of the plug into the housing, and that, in the radial direction, exerts a contact pressure against the plug, and means for releasing the locking means by an external force on the elastic element, to neutralize said retaining force and thereby permit a removal of the plug from the housing, wherein said elastic element is a U-shaped leaf spring having a first branch and a second branch and a central region, the first and second branches of the U being elastically connected to the central region of the U-shape with the first branch of the U extending from the central region in a direction forming a first angle to the axis of insertion, and the second branch extending from the central region forming a second angle to the axis of insertion, wherein the end of one of the first and second branches is a free end having a flange, the first and second branches having respective first and second holes, the first and second holes having respective dimensions that allow the plug to be inserted through the first and second holes in the housing, said elastic element being deformable between:

the free state, in the absence of an inserted plug, in which the projections of the first and second holes in a plane perpendicular to the axis of insertion are overlapping but misaligned, and the deformed state, in the presence of an inserted plug, in which the projections of the first and second holes in the plane perpendicular to the axis of insertion are aligned so that an edge of each of the first and second holes contact the plug inserted therein and exert through a reaction effect of the deformed leaf spring, a radial stress force against the plug, producing said contact pressure, and wherein the generator comprises an electrical connection terminal and the leaf spring comprises a metal blade connected to the electrical connection terminal, so as to simultaneously achieve the mechanical immobilization of the plug in the housing and the electrical connection of the plug to the electrical connection terminal.

10. The device of claim 9, wherein the flange comprises a flattened pushbutton extending in a plane substantially parallel to the axis of insertion.

11. The device of claim 9, wherein the connector head further comprises an internal cavity isolated from the external environment and the flange extends into the internal cavity.

12. The device of claim 9, wherein the flange comprises an element causing a tactile response to the change of state between the free and deformed states.

13. The device of claim 9, wherein the end of the other of the first and second branches is a stationary end relative to the connector head.

14. The device of claim 13, wherein a resilient elastic auxiliary member is interposed between the connector head and the central region.

15. The device of claim 9, wherein:

the end of the other of the first and second branches is a moving end for pivoting, relative to the connector head, around an axis perpendicular to the axis of insertion, and a resilient elastic member is interposed between the connector head and the central region of the U.

16. The device of claim 9, wherein the first branch extends along a plane that is substantially perpendicular to the axis of insertion.

17. The device of claim 9, wherein the second branch extends along a plane that is substantially oblique to, forming an angle in a range selected from between 45° and 75° from, the axis of insertion.

* * * * *